US006897452B2

(12) United States Patent
McDonald et al.

(10) Patent No.: US 6,897,452 B2
(45) Date of Patent: May 24, 2005

(54) APPARATUS FOR IRRADIATING MATERIAL (75) Inventors: Austin McDonald, Raritan, NJ (US);
Gerhard Leipold, Watchung, NJ (US)

(73) Assignee: G. A. Apollo Limited, Dublin (IE)

( * ) Notice: Subject to any disclaimer, the term of this patent is extended or adjusted under 35 U.S.C. 154(b) by 0 days.

(21) Appl. No.: 10/275,238

(22) PCT Filed: May 3, 2001

(86) PCT No.: PCT/IE01/00059

§ 371 (c)(1),
(2), (4) Date: Mar. 3, 2003

(87) PCT Pub. No.: WO01/85335

PCT Pub. Date: Nov. 15, 2001

(65) Prior Publication Data

US 2003/0155524 A1 Aug. 21, 2003

(30) Foreign Application Priority Data

May 5, 2000 (IE) .......................................... S2000/0339

(51) Int. Cl.[7] .................................................. A61L 2/10
(52) U.S. Cl. ..................... 250/437; 250/438; 250/461.1; 250/495.1; 250/504 R; 250/369; 250/372; 422/24
(58) Field of Search .......................... 313/29, 163, 328; 250/437, 438, 461.1, 495.1, 504 R, 369, 372, 237; 422/24

(56) References Cited

U.S. PATENT DOCUMENTS

| 3,659,096 A | * | 4/1972 | Kompanek | .................... | 422/24 |
| 4,837,484 A | * | 6/1989 | Eliasson et al. | ............ | 313/634 |
| 4,956,754 A | * | 9/1990 | Chen | .......................... | 362/101 |
| 4,971,687 A | * | 11/1990 | Anderson | ..................... | 210/85 |
| 4,983,881 A | * | 1/1991 | Eliasson et al. | ............ | 313/607 |
| 5,666,026 A | * | 9/1997 | Matsuno et al. | ............ | 313/634 |
| 5,722,761 A | * | 3/1998 | Knight | ......................... | 362/96 |
| 5,757,132 A | * | 5/1998 | Matsuno et al. | ............ | 313/607 |
| 5,874,741 A | * | 2/1999 | Matschke | .................... | 250/435 |
| 6,042,909 A | * | 3/2000 | Dunleavy et al. | .......... | 428/35.7 |
| 6,113,566 A | * | 9/2000 | Schleicher | ................. | 604/6.08 |
| 6,373,192 B1 | * | 4/2002 | Morimoto et al. | .......... | 313/607 |
| 6,501,079 B1 | * | 12/2002 | Furuya | ....................... | 250/437 |
| 6,552,351 B2 | * | 4/2003 | Vitt | ............................. | 250/435 |
| 6,590,217 B1 | * | 7/2003 | Freeman et al. | ............ | 250/435 |
| 6,614,028 B1 | * | 9/2003 | Cekic et al. | ................ | 250/435 |
| 6,633,109 B2 | * | 10/2003 | Falkenstein | .................. | 313/29 |

* cited by examiner

Primary Examiner—Nikita Wells
Assistant Examiner—Johnnie L Smith, II
(74) Attorney, Agent, or Firm—Edward W. Callan (57) ABSTRACT An apparatus (1) for irradiating material comprises a single UV, pulsed brigth white light or IR lamp (2) with a centrally disposed receptacle (3) for containing material to be irradiated. The lamp can be an elongate hollow tube (2) of annular construction. Internal formations may be present within the lamp to control the position of the arc. For example, the lamp may have a plurality of longitudinal segments arranged such that a discharge arc is formed within each segment or internal formations may be provided to direct the position of the arc within the lamp. A pump (36) may be included for moving material through the receptacle which is preferably the hollow area within the annulus of the elongate hollow tube. Material can be treated batchwise or in a continuous process. This apparatus is suitable for the sterilisation of biological and/or non-biological materials. A further use is in carrying out photolysis on chemical substances in photochemical reactions.

13 Claims, 9 Drawing Sheets

APPARATUS FOR IRRADIATING MATERIAL

The present invention relates to an apparatus for irradiating material and particularly to an apparatus which emits visible light or UV radiation.

Pulsed white light and ultraviolet light have well documented properties as sterilising media. Visible and UV light is extensively used in the chemical field, both industrial and research, as an energy source useful in conducting photochemical reactions. However, for such reactions using known methodology, complex means must be employed to ensure that all reactant receives the same light exposure and it is difficult to control the reaction to limit the further light-induced reaction of desired product into undesired by-product.

GB 695,541 discloses a method of treating products with electro-magnetic energy. In an example given, blood serum is supplied to the inner surface of a fast rotating vertical cylinder. The serum enters the cylinder at an upper portion and after treatment is led away from a lower portion of the cylinder. Centrifugal force is applied so that a film of serum is held against the walls of the cylinder. At the axis of the cylinder is a quartz mercury vapor lamp, which illuminates outwardly to irradiate the serum as it passes through the cylinder.

CN 1 073 106 discloses an apparatus which can be used to irradiate blood with ultraviolet light. The light is passed through a spiral quartz tube and is irradiated by an ultraviolet tube lamp housed in the centre of the spiral quartz tube.

EP 0 198 212 discloses a method for the physiologically and therapeutically effective irradiation of venous blood. The document describes an apparatus which comprises a housing which encloses an irradiating emitter and a pair of reflectors. A PVC hose passes through the housing and carries the liquid which is to be irradiated.

U.S. Pat. No. 3,894,236 discloses a device for irradiating fluids comprising a housing which surrounds an elongated ultra-violet lamp, there being a closed annular space located between the housing and the lamp. The closed annular space provides a passageway through which fluids can pass to be irradiated. The relatively thin flattened passageway surrounds the ultraviolet lamp and either encircles or extends longitudinally about the lamp. The passageway may provide several separate paths for sterilization of different fluid streams.

None of the above documents provide a reliable means by which a controlled dose of radiation can be delivered to a sample material. In general, these documents relate to a light source which irradiates outwardly to impinge on a sample, with the disadvantage that sample nearer the source receives a higher dose than sample further away.

JP 10 151453 discloses an ultraviolet irradiation water-treatment apparatus. The treatment apparatus comprises a cylinder with an inlet and outlet for the water being treated. The cylinder interior has a plurality of elongate UV lamps placed in parallel about its circumference with the longitudinal axes of the lamps arranged in the direction of flow. In effect the lamps appear to be arranged as an annulus and their combined effect is to irradiate inwardly so as to sterilise water flowing through that annulus. This apparatus is complex.

JP 5 217 552 discloses an ultraviolet ray radiation device. The apparatus comprises a mercury discharge lamp fitted with a U-shaped luminous bulb. The discharge space of the bulb is an almost rectangular flat shape. Utilising reflecting bodies enables this instrument to provide a superior, uniform, high-density output. However, this apparatus is not hollow and it is complex.

Also known is the RAYONET "Merry go Round" apparatus available for conducting photochemical reactions and which comprises a central UV lamp surrounded by a rotating carousel for holding tubes containing reactant. The carousel rotates relative to the lamp so that all tubes receive an even distribution of light. Furthermore, means are provided for rotating the tubes about their longitudinal axes further to ensure evenness in the exposure of each tube to the UV radiation. This apparatus is complex.

The present invention seeks to alleviate the problems of the prior art described above and to provide a simpler apparatus for delivering a controlled dosage of radiation, particularly visible light or UV irradiation, to a sample material.

Accordingly, the present invention provides an irradiation apparatus comprising a light emitter for ultraviolet light, infrared light or pulsed bright white light in the form of a single linear lamp of annular construction having a centrally disposed hollow area, and a receptacle for containing a material to be treated by irradiation, the receptacle being surrounded by and positioned within the hollow area of the lamp, wherein the receptacle includes a passage through which material can flow or be pumped in a defined path of travel, and wherein the passage does not contain anything that can prevent all of the material in the passage from being subjected to a predetermined desired dosage of radiation. In one preferred arrangement which is particularly suitable for sterilizing a medium, the emitter is an ultraviolet lamp. The apparatus may also include pump means for moving material through the passage for treatment.

In one preferred arrangement, the lamp is formed as an elongate hollow tube preferably of an annular construction. Internal formations may be provided within the lamp to provide a means of controlling the position of the arc within the lamp on energising the lamp. A particularly preferred arrangement includes a lamp which has a plurality of longitudinal segments arranged side by side and arranged that a discharge arc may be formed within each segment.

The lamp of the invention can be constructed to emit light of any desired wavelength of the spectrum. This is possible by means well known in the art including choice of appropriate filament, filament coating, gas type, gas pressure and so on. The intensity of radiation delivered can also be altered by known means such as varying the distance between the light source and the target.

As used herein, the term "lamp" is to be understood to refer to a single bulb or light source or light emitter.

Various materials may be treated in the apparatus of the invention and the apparatus may be scaled-up or down depending on the volume of material to be treated. Exemplary materials which may be treated include water in water-purification applications, aqueous liquids and other gaseous and non-gaseous fluids including but not limited to pharmaceuticals, foods and drinks where sterility is required or desirable. Material may be treated batchwise or in a continuous process. In principle, any material which is flowable or pumpable may be subjected to treatment in the apparatus of the present invention in a continuous process.

In particular, the apparatus provides an effective means for treating biological fluids or material such as blood serum or other blood products which include valuable proteinaceous materials required by a patient in need thereof. One example of such material comprises blood-clotting factors and many other biologically valuable materials will suggest themselves to the skilled person. It is an ever-present concern for patients in need of such products that they may derive from donors whose blood is contaminated with infectious agents such as hepatitis, HIV or other viruses or biological contaminants. The present invention provides a new and effective means for pre-treating such products prior to administering them to a patient. Nucleic acids are well known to be susceptible to be damaged by UV light and pulsed white light. In the case of UV the known optimal killing frequency is around 260 nm and when light of this wavelength is employed for a sufficient length of time, total killing of infectious contaminants such as bacteria, spores, parasites and viruses may be achieved. On the other hand, since generally speaking proteins have low absorption of light in the ultraviolet range, they are left unaffected by the UV irradiation treatment.

Since the light is directed inwardly toward the sample to be sterilised, effective radiation dosage can be reliably directed to all of the sample to achieve sterilisation.

Another application of the apparatus of the invention lies in the field of photochemical reactions, carried out by the photolysis of chemical substances either alone or in mixtures, with or without the presence of a solvent and/or a photosensitiser. Such reactions include but are not limited to photocycloaddition reactions, photochemical rearrangement processes and photochemical cleavage reactions. It is currently a limitation of such reactions that they can be difficult to control to obtain the desired products with minimum contamination from unreacted starting compound or from unwanted product derived from further reaction of the desired primary product. These effects occur as a result of uneven exposure to radiation, since such reactions are conducted in batches and therefore, there is often an uneven exposure of reactant to the light, since sample further from the source receives less light than sample nearer the source. Further, elongating the exposure time so as to increase the amount of reactant which receives a sufficiency of energy to react can have the detrimental effect of causing desired product to react further to form an undesired product.

Since in a preferred arrangement the apparatus of the present invention includes a light source which irradiates axially inwardly to impinge upon material residing in the vicinity of that axis, the whole of the material can be subjected to a predetermined desired dose of radiation. In addition, since the material can be caused to travel through the irradiation zone by gravity flow or pumping, it is possible to carry on a continuous treatment whilst controlling the treatment by controlling the residence time of any portion of the material to be treated or reaction mixture within the irradiation zone. Thus, preliminary experimentation can be undertaken to determine the dose and duration of exposure which achieves total sterilisation or optimises the yield or desired product as the case may be. Subsequently, in a scale-up treatment or reaction in the apparatus of the invention, the material can be continuously pumped through at the predetermined rate so as to obtain the desired sterilisation or the optimal yield of product in the outflow from the irradiation zone.

By the use of the apparatus according to the invention, a fluid to be treated is led though a defined path of travel and subjected to a defined radiation intensity and wavelength to obtain a predictable exposure of the entire sample. The exposure time can easily be varied by altering the flow rate of the sample. Conveniently a pump such as a peristaltic pump can be used to control the flow rate. Whilst continuous processes are very useful, it will be appreciated that the invention is not limited to such processes and that batch treatments can equally be used with the apparatus of the invention.

The invention will now be described more particularly with reference to the accompanying drawings which show, by way of example only, several embodiments of an irradiation apparatus of the invention.

In the drawings:—

FIG. 4c is a side sectional view of a variation of the lamp of FIG. 4a;

Figure 1:
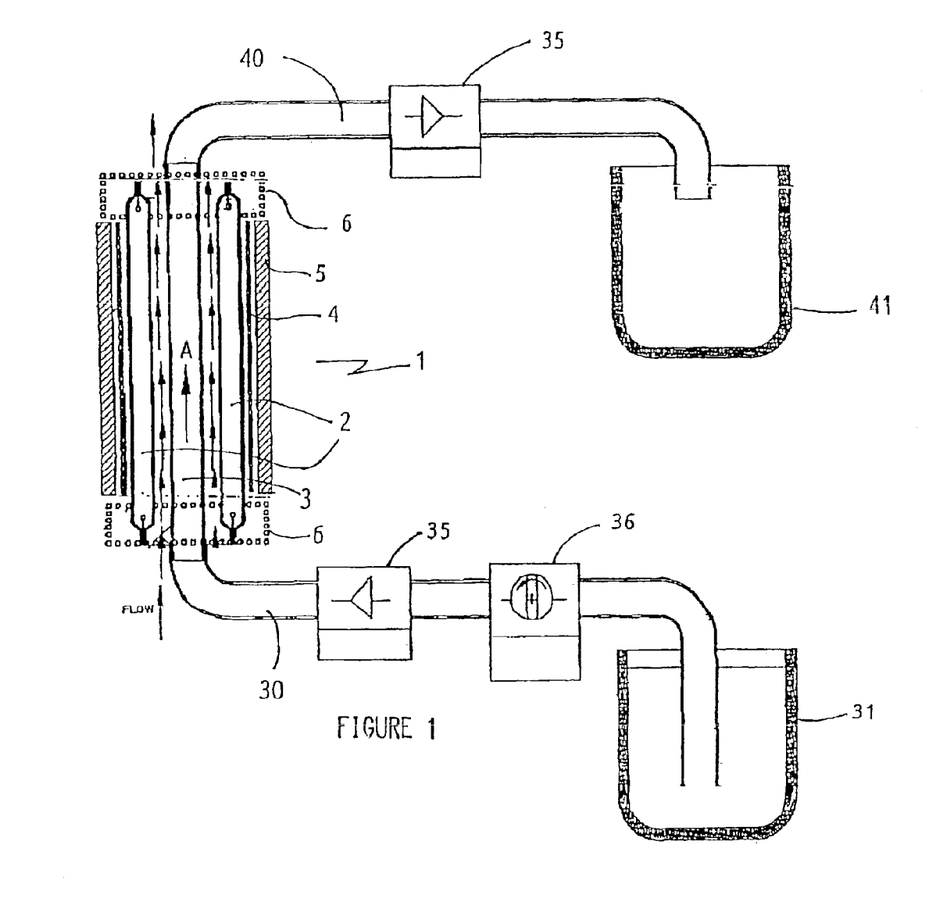
FIG. 1 is an elevation view in partial section showing one embodiment of an apparatus according to the invention.

Referring initially to FIG. 1, an apparatus according to the invention is shown. This comprises a reactor 1 for irradiating a sample which is conducted through supply line tubing 30 from sample reservoir 31 into the reactor 1. Following irradiation, the treated sample is conveyed away from the reactor 1 via tubing line 40 to sample reservoir 41. Both tubings 30 and 40 have a check valve 35 in the line to enable control to be achieved over the possible inadvertent mixing of untreated and treated sample. The apparatus shown in FIG. 1 is intended for use in a continuous treatment process and consequently a pump 36 is provided in the supply line 30. Any suitable pump may be used, for example a peristaltic pump. Alternatively, the pump may be placed on the other side of the reactor in tubing 40. In suitable cases, the sample may be supplied to the top of the reactor to fall under gravity through the reactor.

The choice of tubing 30,40 will be made on the basis of the nature of the sample to be treated. For biological applications, it may often be possible to use flexible tubing such as silicone tubing or the like. Other applications may require other types of material to be used. For example some chemical processes may be of a nature that inert tubing is needed, such as a vitreous material which is transparent to light of the frequency of interest.

Reactor 1 comprises a radiation source which in this case is an ultraviolet lamp 2 which is formed as an annular sleeve to surround a sample vessel 3. Lamp 2, shown in section, is an elongate hollow cylinder which has an axially disposed hollow passage 20 at its centre into which vessel 3 fits, the arrangement being such that the longitudinal axes of the lamp 2 and vessel 3 are concentric. Thus, lamp 2 is in effect an annular sleeve surrounding the vessel 3. Located axially radially outwardly of the lamp 2 is a reflector 4 which serves to reflect light emitted by the lamp 2 axially inwardly. Finally, the whole is surrounded by a shield 5 which serves to prevent light from escaping the reactor 1 and further optionally serves as a conduit for cooling fluid from upper and lower cooling chambers 6. Cooling chambers 6 may also supply cooling fluid for circulation between the lamp 2 and vessel 3 for controlling the temperature within the reactor 1, preventing overheating and flushing out any undesired ozone build-up. One circulation arrangement is shown by the arrows. The cooling fluid will be selected to meet requirements and may comprise, as an example, an inert gas.

Each lamp produces radiation of a specific desired wavelength. Vessel 3 is fabricated from quartz, which is transparent to UV light. When the lamp required is other than a UV one, then the vessel will be fabricated from a suitable material which is transparent to light of the desired frequency generated by the lamp being used. Generally, vitreous tubing will be suitable for this purpose.

Tubing 30,40 is connectable to vessel 3 by pushing the flexible tubing over the end of the vessel 3. In the case of a rigid tubing, an appropriate coupling will be used to secure the parts together.

Vessel 3 is arranged to be supported within the hollow 20 of lamp 2 by fixtures which are not shown. Most preferably, vessel 3 is removably housed within the hollow of the lamp and can be readily disengaged therefrom for cleaning or maintenance and remounted concentrically In use, sample to be treated is placed in reservoir 31 and lamp 2 is energised. Once the lamp 2 has warmed up, pump 36 is activated and valves 35 are opened. Sample is then pumped in the direction of the arrow A through tubing 30 and into vessel 3. As the column of fluid sample rises through vessel 3 at a pre-determined rate which is selected to control the dosage of irradiation received by each part of the sample, the sample enters the irradiation zone, where it is surrounded by the lamp 2. As it passes into the vessel 3 from its base, it enters the central portion of the vessel 3 intermediate its ends and the ends of the lamp 2, this being the area of maximum and constant lamp discharge. As the residence time within this part of the vessel 3 is controlled by the bore size of the vessel 3 and the rate of flow of the sample, it can readily be arranged that sample resides within this area of the vessel 3 for a time sufficient to obtain the dosage desired.

Cooling liquid or an inert gas is constantly passed through the reactor 1 to maintain the reactor at a desired temperature.

After passing through the reactor 1, treated sample is led away via tubing 40 to reservoir 41, which may be a test tube, sterilised container or any other suitable receptacle.

In the case of a biological sample, the aim of the passage through the reactor 1 is to sterilise the sample. In the case of a chemical reaction, the aim will be to enable a photochemical reaction to occur. In either case, check valves 35 can be used alone or in combination to prevent cross-contamination occurring between treated and untreated sample.

Whilst vessel 3 has been described above as a hollow tube for receiving a column of liquid, it will be appreciated that the gauge of the bore can be selected to suit the intended purpose and can vary from a capillary tube to a large bore for industrial preparative applications. Other adaptations are also possible and for example, the vessel need not be circular in cross-section, but may have other shapes. It may be used in such a way as to create a thin film of sample on its interior wall or it may be arranged with two or more internal channels for the same or different sample streams.

Alternatively, the vessel 3 and reactor 1 may readily be adapted for batch treatment of a sample, in which case tubings 30,40 values 35, pump 36 and reservoirs 31,41 will not be required.

Figure 2A:
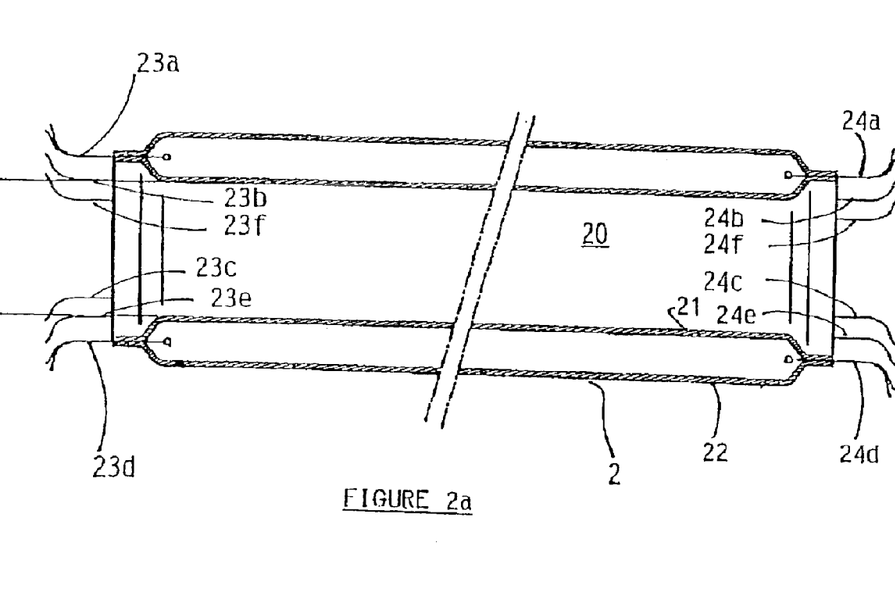
FIGS. 2a and 2b and side and plan sectional views in more detail of the lamp of FIG. 1.
Figure 2B:
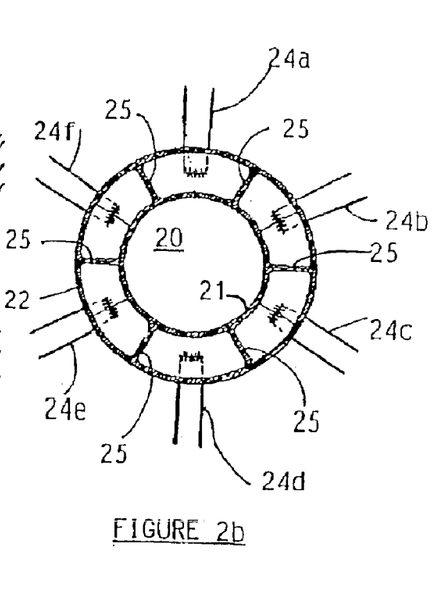

An embodiment of lamp 2 will now be described more particularly with reference to FIGS. 2a and 2b. Lamp 2 is an ultraviolet discharge lamp with an annular cross-section, as shown in FIG. 2b. The hollow area 20 of the lamp 2 receives the sample vessel 3 axially within it. Lamp 2 has quartz inner and outer walls 21,22 respectively. Six filaments 23a–f, 24a–f are provided at each end of the lamp and the whole is filled with mercury vapour and sealed. As seen in FIG. 2b, which depicts the end of the lamp at which filament 24a–f are located, the six filaments 24a–f are deployed about the interior of the annular space between the inner wall 21 and outer wall 22. A similar arrangement of six filaments 23a–f is provided at the opposite end of the lamp filaments. On energising the filaments, an arc is formed between each pair of filaments (23a, 24a), (23b, 24b), (23c, 24c) etc. causing the mercury vapor to discharge. The precise frequency of the emitted energy can be selected by means well known to those skilled in the art. Since the position of each arc within the lamp could vary, the lamp is provided with six interior walls 25 which are spaced apart about the interior circumference of the lamp and extend between the inner and outer walls 21,22 and along the length of the lamp to separate the interior of the lamp into six, elongate sections, each section having a filament pair at either end. Once the arc is established in one of the sections between its filament pair, it will remain in that section so that a steady output is provided from the lamp. Thus, when an arc is established in several sections concurrently, the lamp acts as a series of connected lamps, all emitting in the same fashion. The number of sections provided is not critical and any number between three and twelve can be employed, with a higher number being prepared.

Lamp 2 may be formed by fabricating the inner wall 21 with the interior walls 25 formed as fins extending axially outwardly therefrom. Outer 22 is formed as a sleeve to fit over inner wall 21 and walls 25, so that the free ends of walls 25 form a tight fit with the inner side of outer wall 22. Subsequently, the whole is sealed together, preferably in such a way that so far as possible, each section is isolated from each other section.

FIGS. 3 to 8 show alternative embodiments of lamps according to the invention, which differ from the lamp described above in that no sections are provided internally in the lamp and in that different ways of introducing the filaments into the lamp are used. In these embodiments each lamp has only one pair of filaments for producing an arc between them.

Figure 3A:
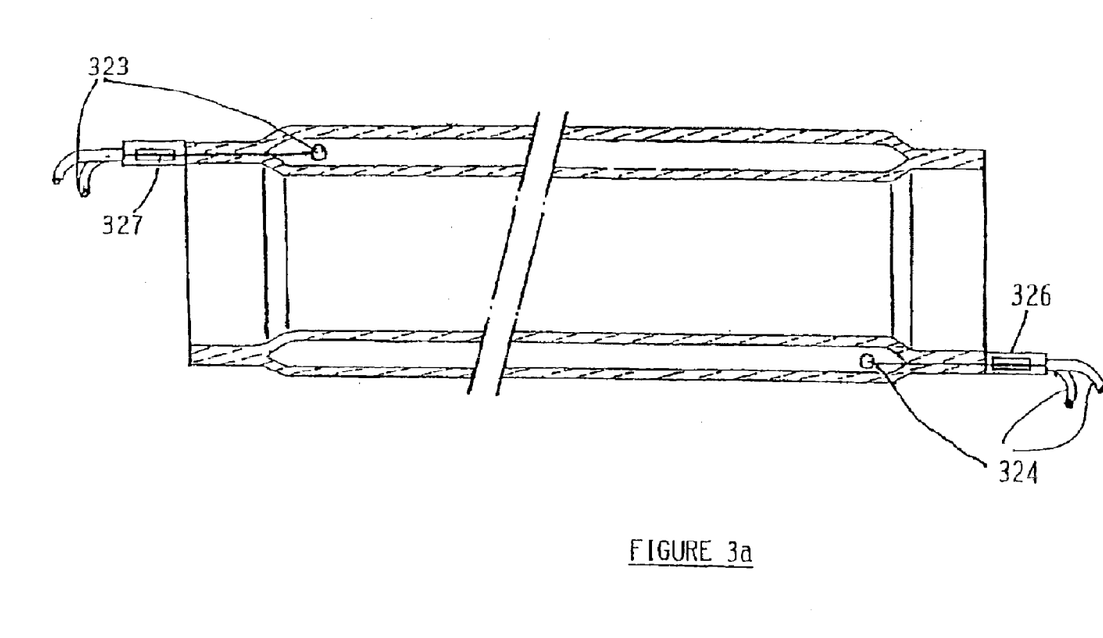
FIGS. 3a and 3b are side sectional and plan views respectively of an alternative embodiment of a lamp.
Figure 3B:
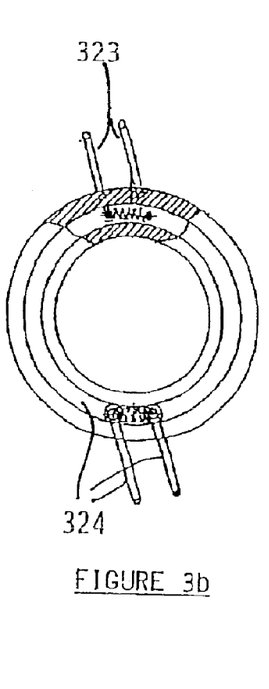

In FIG. 3, each filament 323 and 324 is led in and out through openings 326, 327 at either end of the lamp and the openings, which are co-axial with the longitudinal axis of the lamp, are disposed on opposite sides of the lamp.

Figures 4A, 4B:
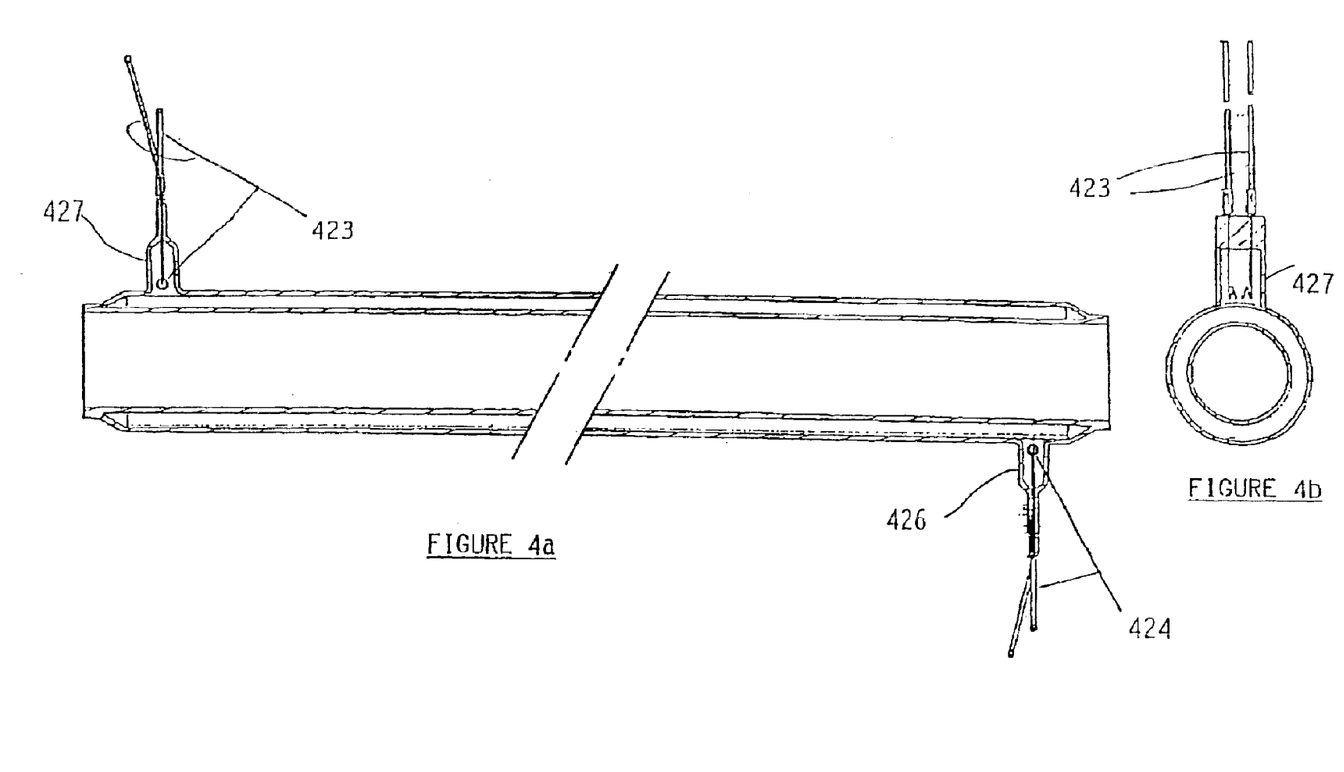
FIGS. 4a and 4b are side sectional and plan views respectively of a further embodiment of a lamp.
Figure 4C:
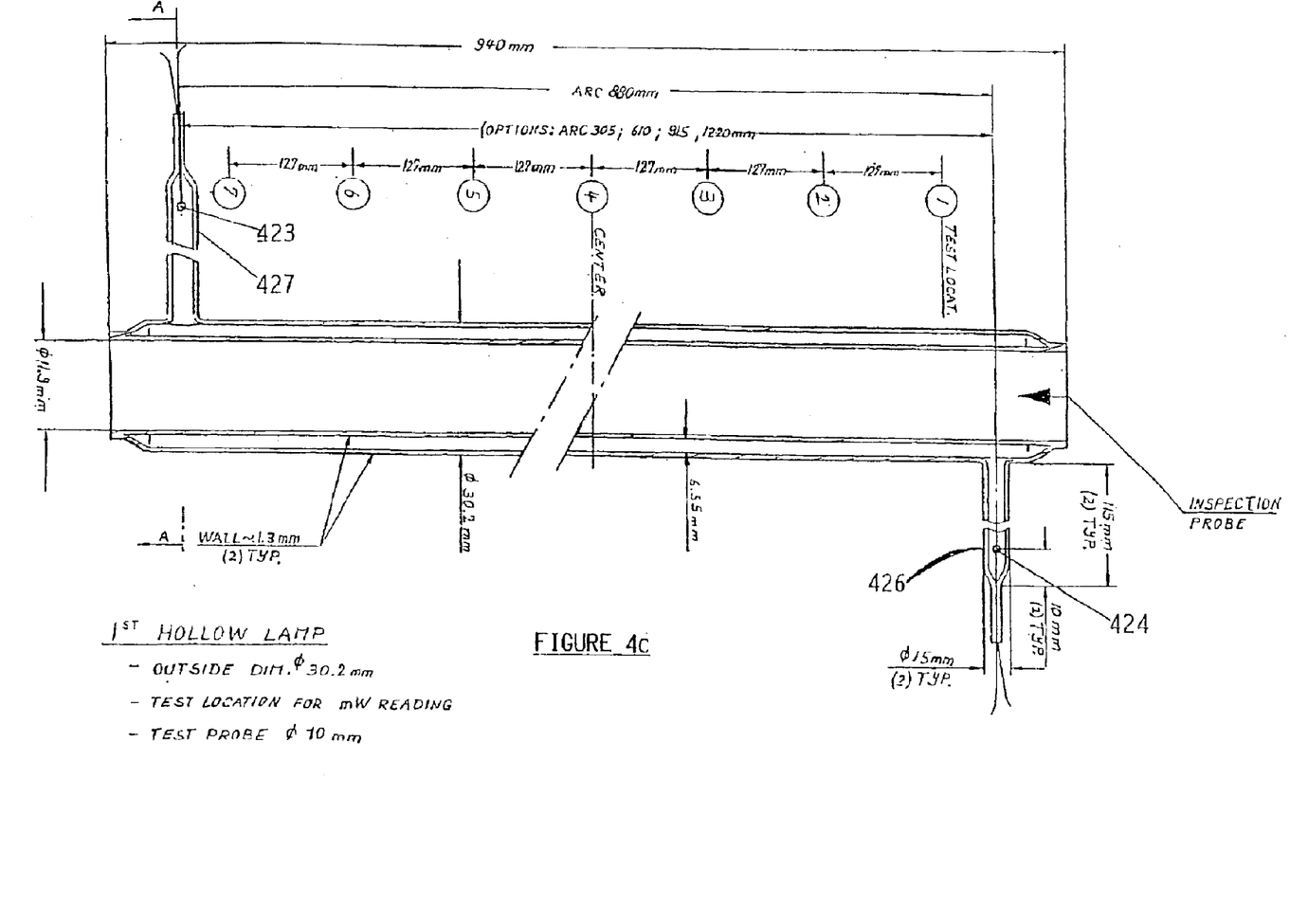

A preferred embodiment shown in FIG. 4 has a similar arrangement to that of FIG. 3, with the difference that the openings 426, 427 for filaments 423, 424 are perpendicular to the longitudinal axis of the lamp. FIG. 4c shows a lamp which is identical in all material respects to that of FIGS. 4a and 4b, differing only in immaterial details. The lamp of FIG. 4c was used to test the uniformity of light intensity generated along the length of the lamp. The dimensions of the lamp are shown in FIG. 4c by way only of one specific example. It will be appreciated that the exact shape, dimensions and type of the emitter can be varied to suit the particular requirements of a system designed for a particular purpose. The particular lamp of FIG. 4c was designed as a low-pressure mercury vapour lamp emitting at 254 nm. A test probe to measure intensity of UV light generated by the lamp in milliwatts was constructed with a diameter of 9.5 mm. The probe was lowered into the 11.3 mm hollow of the lamp and readings were made at 7 points along the lamp at approximately 127 mm intervals, point 4 being the longitudinal centre of the lamp and points 1 and 7 being near the opposed ends of the lamp.

| | |
|---|---|
| Power settings: | lamp power approximately 184 V. |
| ARC: | 8.8 cm |
| Wavelength: | 254 nm |

Results

It was observed that the intensity drop from point 4 to point 7 was approximately the same as the intensity drop from point 4 to point 1. The average intensity readings were about 18 mw to 11 mw.

Figures 5A, 5B, 5C:
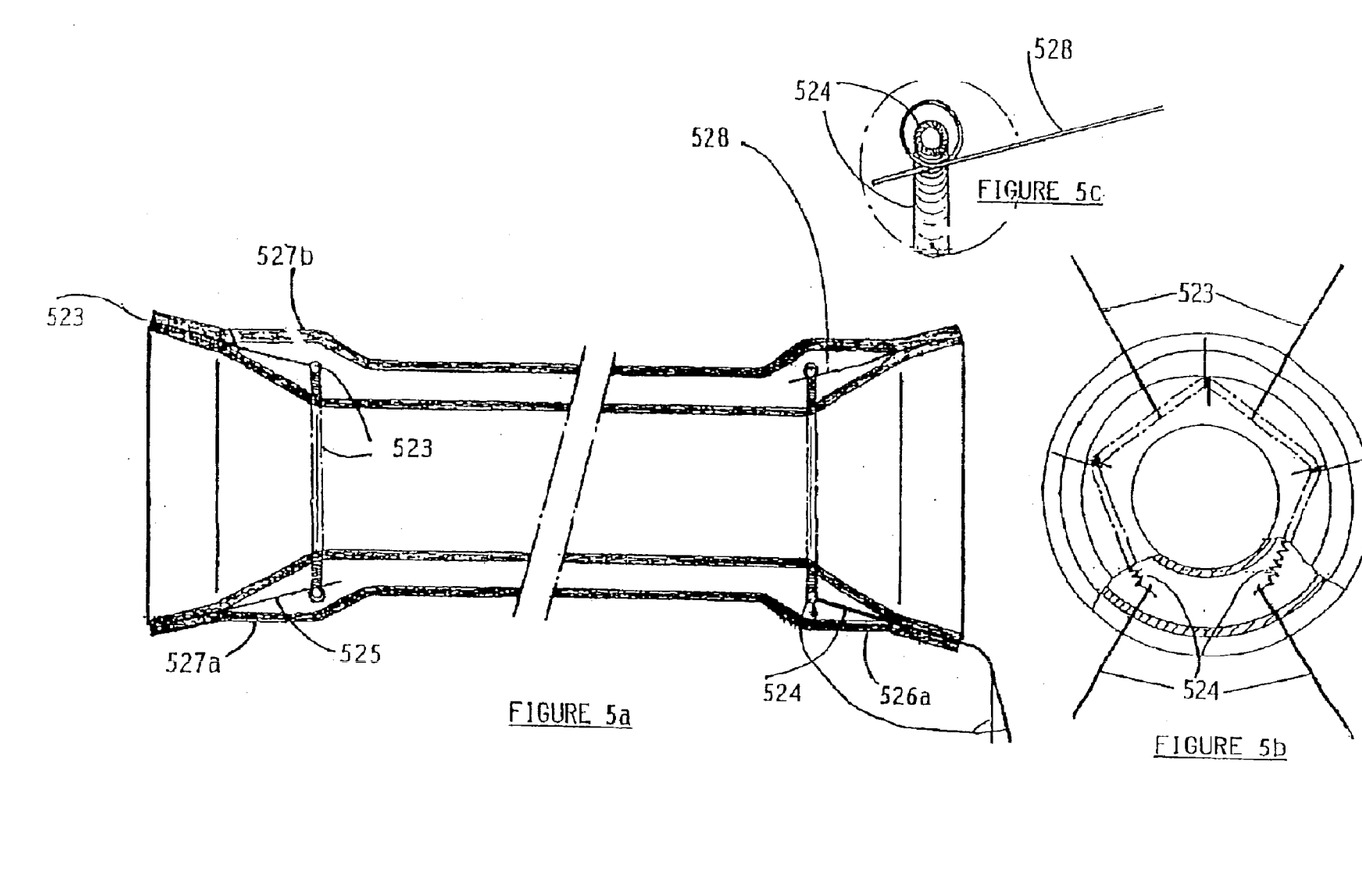
FIGS. 5a and 5b are side sectional and plan views respectively of yet a further embodiment of a lamp and FIG. 5c is a detail showing the suspension of the filament.

FIG. 5 shows yet another arrangement with the openings 526a and b, 527a and b angled outwardly from the longitudinal axis of the lamp and the filaments 523,524 arranged in a substantially hexagonal pattern and hung from a suspension wire 525,528. Filament 523 is led in and out through opening 527b. Filament 524 is let in and out through opening 526a.

Figure 6A:
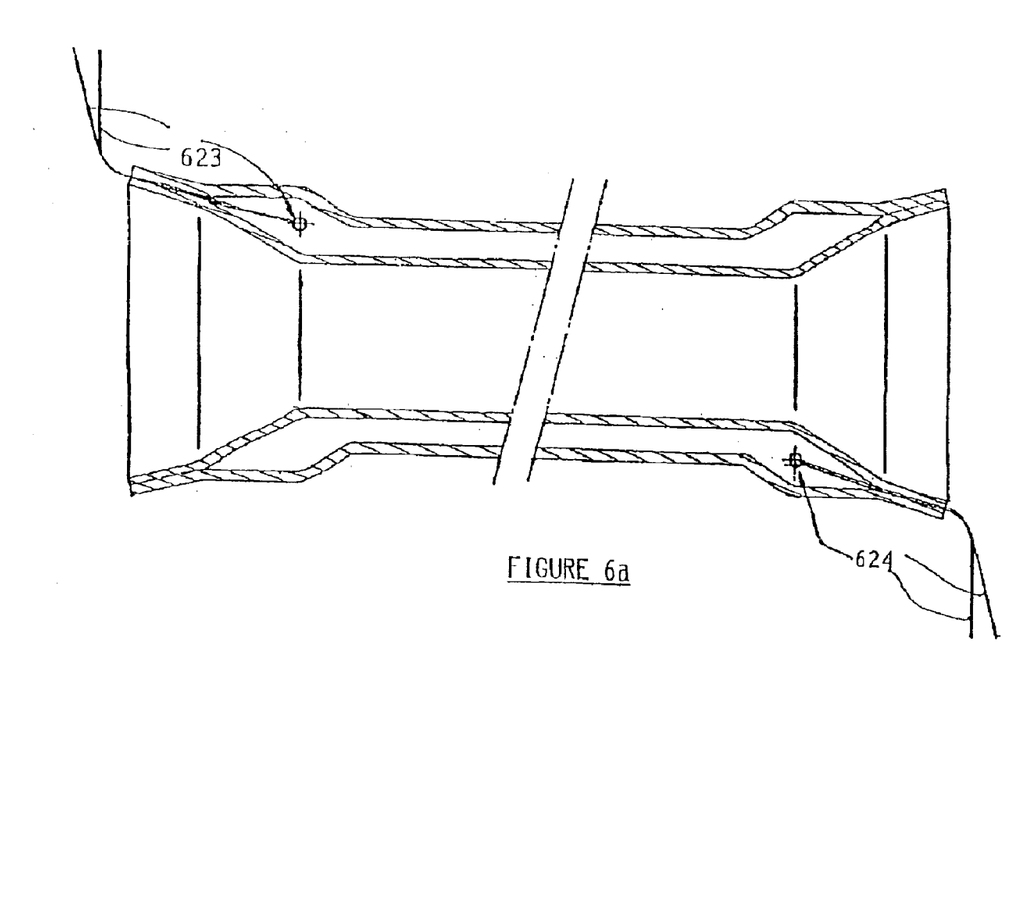
FIGS. 6a and 6b are side sectional and plan views respectively of a yet further embodiment of a lamp.
Figure 6B:
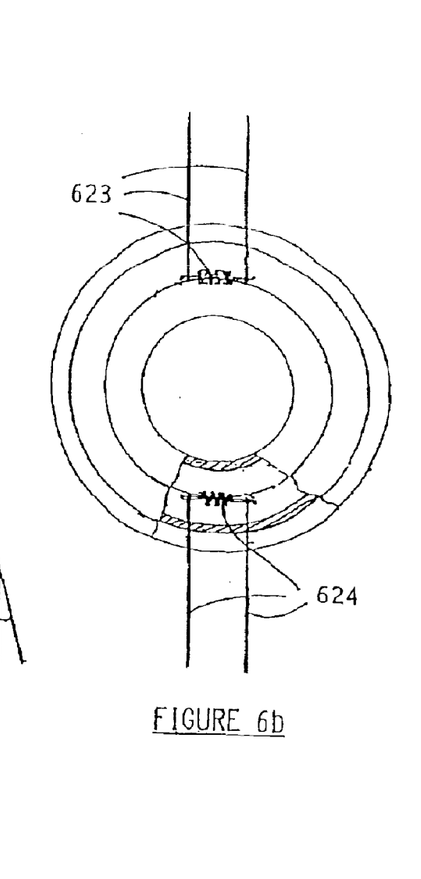

FIG. 6 shows an embodiment similar to FIG. 5, but with the filaments 623,624 arranged as a short filament.

Figure 7A:
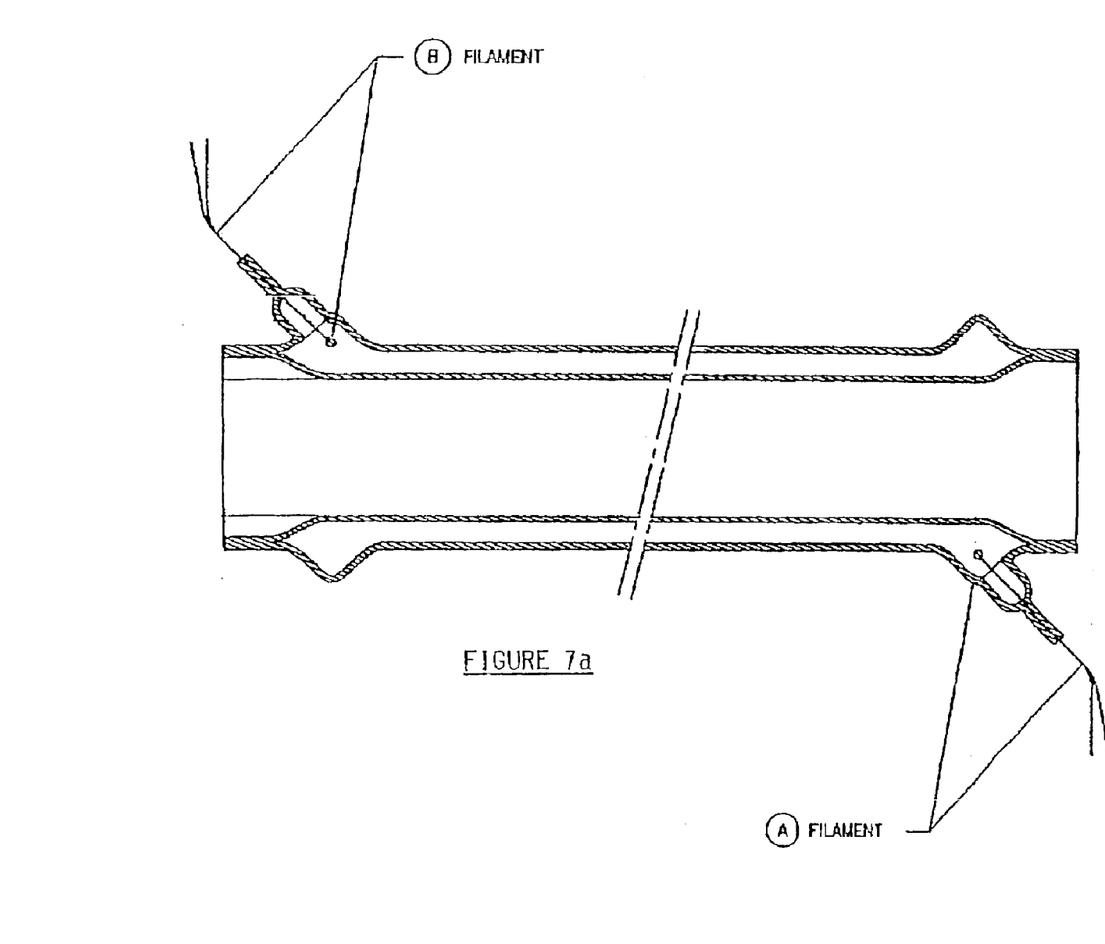
FIGS. 7a and 7b are side sectional and partial sectional plan views respectively of yet another embodiment of a lamp.
Figure 7B:
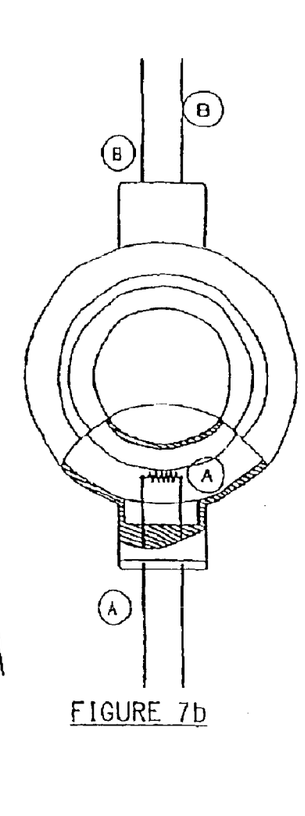

The embodiment of FIG. 7 resembles that of FIG. 6 with the difference that the construction of the openings is slightly different.

Figures 8A, 8B, 8C:
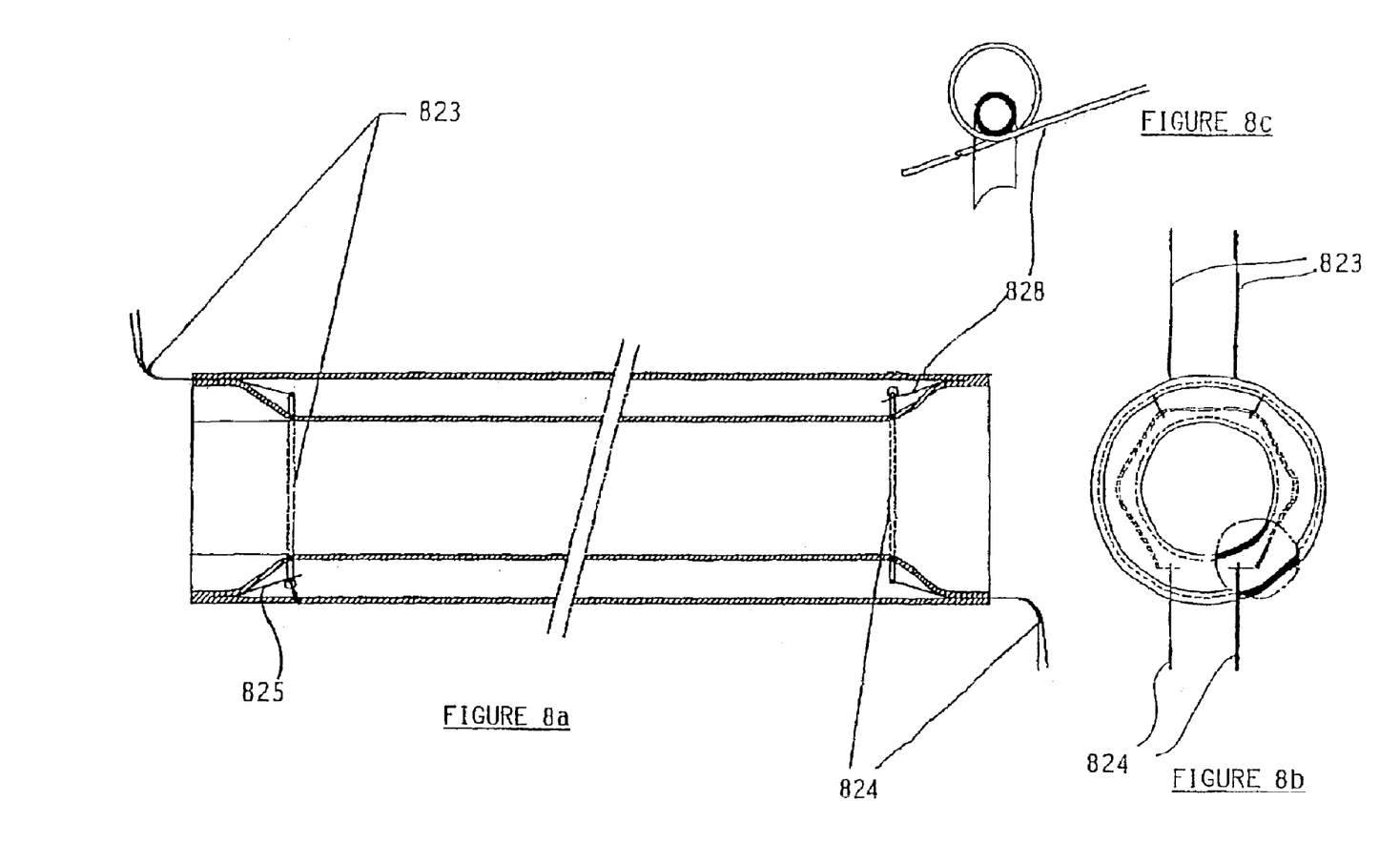
FIGS. 8a and 8b are side sectional and plan views respectively and FIG. 8c is a detail showing the suspension of the filament of a yet further embodiment of a lamp.

Finally, FIG. 8 shows another variation on the arrangement of the deployment of the filaments 823,824 within the lamp, suspended on suspension wires 825,828.

In the embodiments of FIGS. 3 to 8, internal baffles may be provided within the lamp to achieve some degree of control over and stabilisation of the arc. The vapour within the lamp may be electronically or magnetically excited in order to obtain a uniform output from the lamp. In each of these embodiments, a single arc is produced within the lamp when energised.

Whilst the specific description above relates to a UV lamp, it will be apparent to the skilled person that other types of light emitting lamps can be made and used in similar fashion, depending of the light wavelength required.

It will of course be understood that the invention is not limited to the specific details as herein described, which are given by way of example only, and that various alterations and modifications may be made without departing from the scope of the invention as defined by the appended claims.

What is claimed is:

1. An irradiation apparatus comprising a light emitter for ultraviolet light, infrared light or pulsed bright white light in the form of a single linear lamp of annular construction having a centrally disposed hollow area, and a receptacle for containing a material to be treated by irradiation, the receptacle being surrounded by and positioned within the hollow area of the lamp, wherein the receptacle includes an unimpeded passage through which material can flow or be pumped in a defined path of travel, and wherein the passage does not contain any mechanical obstructions which would prevent a direct flow of all materials in said passage from being subjected to a predetermined desired dosage of radiation.

2. An apparatus as claimed in claim 1, in which the lamp is a discharge lamp.

3. An apparatus as claimed in claim 2, in which the lamp has a plurality of longitudinal segments arranged side by side and means are provided for generating an arc within one or more segments.

4. An apparatus as claimed in claim 1, including pump means for moving material through the passage for treatment.

5. An apparatus as claimed in claim 1, in which the light emitter is an ultraviolet light.

6. An apparatus as claimed in claim 1, including cooling means for controlling the temperature of the material to be treated.

7. An apparatus as claimed in claim 1, including a reflective jacket for reflecting the generated light towards the receptacle.

8. An apparatus as claimed in claim 1, including shield means for surrounding the lamp to prevent generated light escaping outwardly therefrom.

9. An apparatus as claimed in claim 1, including means for preventing intermingling of treated and untreated material.

10. A method for sterilising a biological or non-biological sample or for conducting a photochemical reaction on a sample comprising subjecting the sample to light of an effective wavelength within an apparatus as claimed in claim 1.

11. A method according to claim 10 comprising a continuous process in which the sample is continuously passed through the apparatus at a rate effective to sterilise the sample or to enable a desired product to form.

12. Use of the apparatus as claimed in claim 1 for sterilising a biological or non-biological sample, for conducting a photochemical reaction or for otherwise irradiating a material.

13. An apparatus as claimed in claim 1, wherein the receptacle is removably positioned within the hollow area of the lamp.

\* \* \* \* \*